US00PP23545P3

(12) United States Plant Patent
Egger

(10) Patent No.: US PP23,545 P3
(45) Date of Patent: Apr. 16, 2013

(54) ***HEUCHERA* PLANT NAMED 'DELTA DAWN'**

(50) Latin Name: ***Heuchera* hybrid**
Varietal Denomination: Delta Dawn

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 101 days.

(21) Appl. No.: 13/199,585

(22) Filed: Sep. 2, 2011

(65) Prior Publication Data

US 2013/0061361 P1 Mar. 7, 2013

(51) Int. Cl.
*A01H 5/00* (2006.01)

(52) U.S. Cl.
USPC ..... Plt./440

(58) Field of Classification Search ..... Plt./440
See application file for complete search history.

*Primary Examiner* — June Hwu
(74) *Attorney, Agent, or Firm* — Klarquist Sparkman, LLP

(57) ABSTRACT

A new and distinct *Heuchera* plant characterized by leaves which are lime green with red to dark centers in the spring, with centers lightening with age and warmer conditions, medium large, round leaves, creamy white flowers on short flowering stems, medium, mounding habit, and good vigor.

2 Drawing Sheets

Botanical denomination: *Heuchera* hybrid.
Variety designation: 'Delta Dawn'.

BACKGROUND OF THE INVENTION

The present invention relates to a new and distinct cultivar of *Heuchera* and given the cultivar name of 'Delta Dawn'. *Heuchera* is in the family Saxifragaceae. *Heuchera* 'Delta Dawn' originated as part of a planned breeding program for a large leaf, *Heuchera villosa* type with a strong central pattern that holds its color through the summer. This was a cross between *Heuchera* K67-1, a proprietary non-commercial hybrid, as the seed parent, and *Heuchera* K217-6, a proprietary non-commercial hybrid, as the pollen parent.

Compared to the seed parent, *Heuchera* K67-1, the new cultivar is a stronger plant with larger leaves.

Compared to the pollen parent, *Heuchera* K217-6, the new cultivar has red central pattern rather than an all lime colored leaf.

Compared to *Heuchera* 'Miracle' (U.S. Plant Pat. No. 20,274) or *Heuchera* 'Tiramisu' (U.S. Plant Pat. No. 20,439), the new cultivar has larger, rounder leaves, a larger habit, shorter flowering stems, and holds its red center coloration longer, never losing all of it when grown outside in Canby, Oreg.

This new *Heuchera* is uniquely distinguished by:

1. leaves which are lime green with red to dark centers in the spring, with centers lightening with age and warmer conditions,
2. medium large, round leaves,
3. creamy white flowers on short flowering stems,
4. medium, mounding habit,
5. and good vigor.

This new cultivar has been reproduced only by asexual propagation (tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows a one and a half-year-old plant of *Heuchera* 'Delta Dawn' growing in a two gallon container, grown outside in late May in Canby, Oreg.

FIG. 2 shows a plant of the same age growing in the garden in mid June in Canby, Oreg.

FIG. 3 shows a six-month-old plant in bloom grown in a one gallon container in a cold greenhouse in late March in Canby, Oreg.

FIG. 4 shows a comparison of the new cultivar on the left to *Heuchera* 'Miracle' on the right. These plants are the same age and grown in one gallon containers under the same conditions in a cool greenhouse. The photo was taken in late February in Canby, Oreg.

DETAILED PLANT DESCRIPTION

The following is a detailed description of the new *Heuchera* cultivar based on observations taken in late June of one and a half-year-old specimens growing in two gallon containers, grown outside in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, 5$^{th}$ edition.

Plant:

*Form.*—Basal rosette, herbaceous perennial.
*Hardiness.*—USDA Zone 4 to 9.
*Size.*—19 cm tall from top of the foliage to the ground and 39 cm wide.
*Habit.*—Mounding.
*Vigor.*—Good.

Leaf:

*Type.*—Simple.

*Arrangement.*—Rosette.

*Shape.*—Broadly ovate to orbicular.

*Lobing/division.*—5 to 7 shallow lobes, shallow secondary lobes.

*Venation.*—Palmate.

*Margins.*—Broadly crenate.

*Apex.*—Mucronulate.

*Base.*—Cordate, lobes overlapping at the base.

*Blade size.*—Grows to 11.5 cm long and 11 cm wide.

*Surface texture.*—Glandular pubescent on both sides.

*Petiole description.*—Grows to 12 cm long and 3 mm wide, glandular hairs, Green Yellow 1C with tints of Greyed Orange N170C on the sunny side, Greyed Purple 187B at the very base.

*Leaf color.*—Variable depending on temperature and light, with cooler temperatures giving deeper red colors and lower light giving more lime than yellow tones; topside, spring new leaves are Greyed Orange 172A with the edges Yellow Green 151C, bottom side Yellow Green 151C with center tinted Greyed Orange 173C; topside summer leaves Yellow Green N145A with center and along veins Greyed Orange 175A, veins Yellow Green 150D, bottom side Yellow Green 145B; winter leaves topside Yellow 10A with center tinted Greyed Orange 165C, bottom side Yellow Green 145B.

Inflorescence:

*Size.*—Grows to 5 cm wide and 14 cm long.

*Type.*—Thyrse.

*Number of flowers per thyrse.*—About 80.

*Number of thyrse.*—About 5.

*Peduncle.*—Grows to 28 cm long and 3 mm wide at base, Yellow Green 145A, glandular hairs.

*Pedicel.*—1.5 mm to 4 mm, with glandular hairs, Greyed Red 182B.

*Bloom period.*—Occasional blooms May through October in Canby, Oreg.

Flower bud:

*Size.*—2.5 mm wide and 4 mm long.

*Description.*—Glandular puberulent, ovoid, down facing.

*Color.*—Yellow Green 154C.

Flower:

*Type.*—Perfect.

*Shape.*—Campanulate.

*Size.*—6.5 mm long and 5 mm wide.

*Corolla description.*—5 petals, 3 mm long and less than 1 mm wide, spatulate, margins entire, tip acute, glabrous on top and bottom side, White N155B.

*Calyx description.*—Campanulate, 4.5 mm long and 3 mm wide, with 5 lobes divided ½ way to the base, each 1.5 mm wide and 2 mm long, glandular hairs outside and glabrous inside, tip obtuse, margin entire; color both sides Yellow Green 145C.

*Stamen description.*—5 in number, filaments 4 mm long, White N155B, anthers 0.6 mm, Orange Red 31B, pollen Yellow Orange 23A.

*Pistil description.*—1, 2-beaked, 5 mm long and 1.5 mm wide; ovary 1.5 mm long and 1.5 mm wide, Yellow Green 145D; style 3.5 mm long, White NN155B.

*Fragrance.*—None.

*Lastingness.*—Each thyrse blooms for about 3 weeks on the plant.

Fruit:

*Type.*—Two-beaked ovoid capsule.

*Fertility.*—Low.

*Color.*—Greyed Brown 199C.

Seed:

*Shape.*—Linear.

*Size.*—2 mm long.

*Color.*—Black 202A.

Pest and disease tolerance: Excellent disease resistance to powdery mildew, the common problem of *Heuchera*. Susceptible to *Heuchera* rust and root weevils.

I claim:

1. A new and distinct *Heuchera* plant as herein illustrated and described.

* * * * *

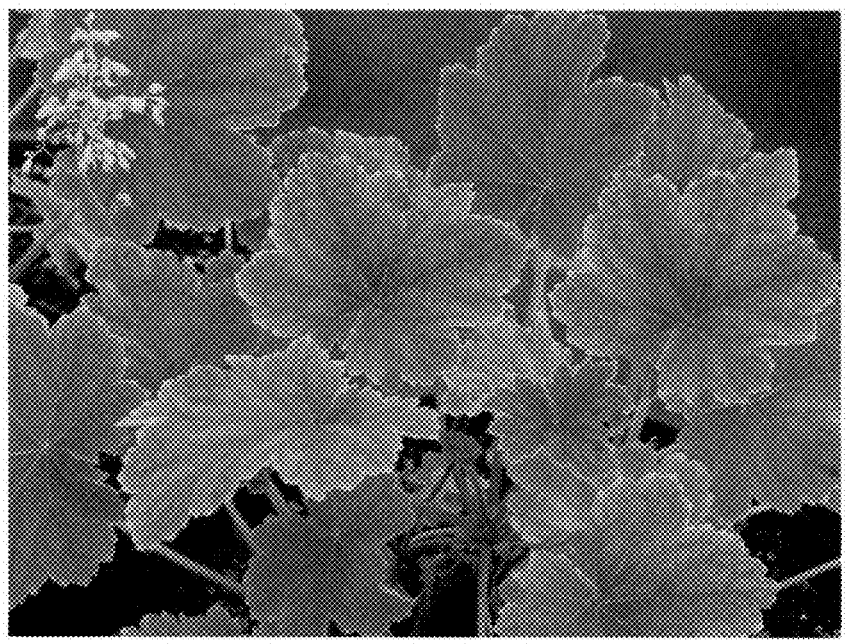
Fig. 1 above
Fig. 2 below
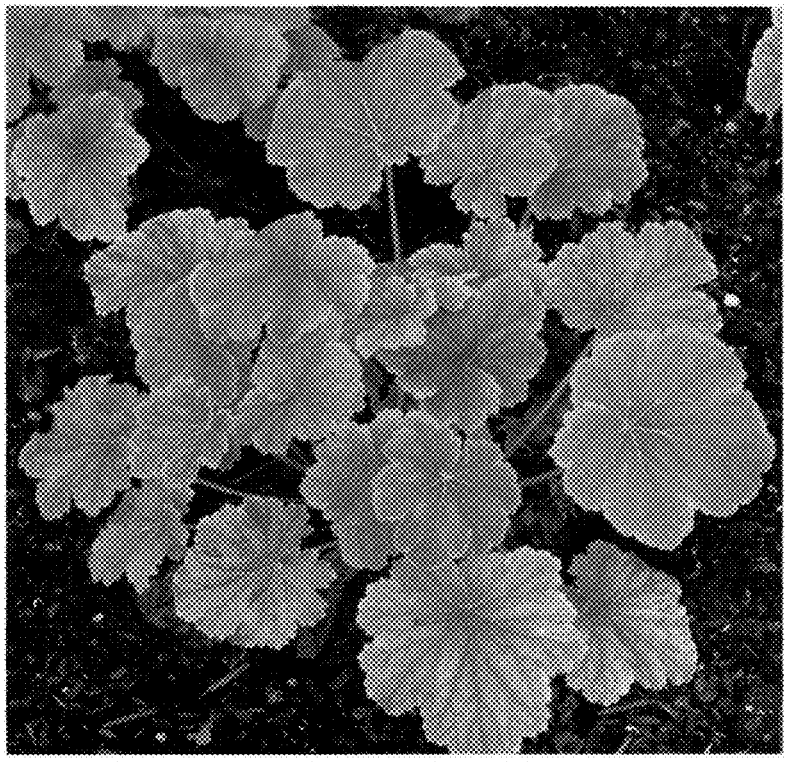

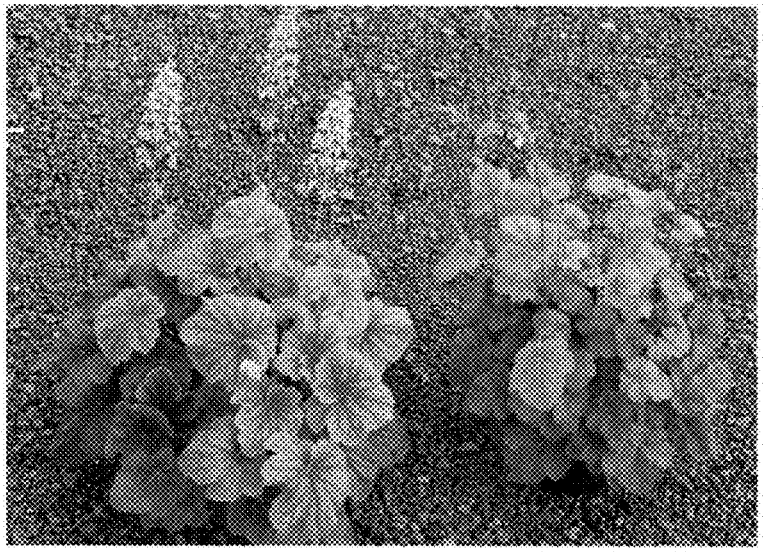

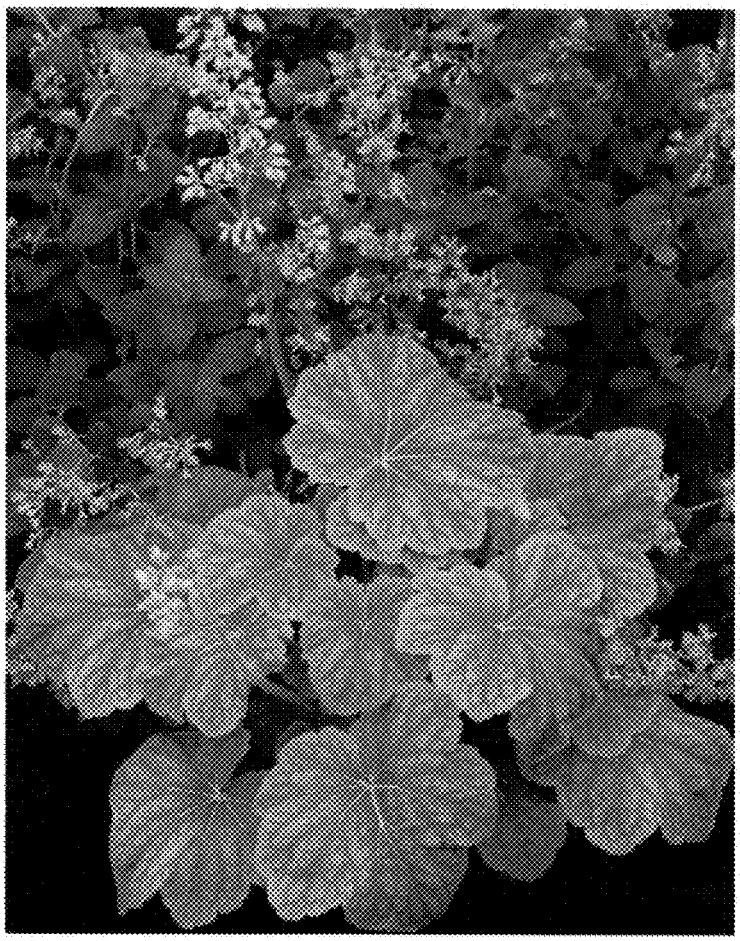
Fig. 3 above
Fig. 4 to right